(12) United States Patent
Matsuda et al.

(10) Patent No.: US 9,464,257 B2
(45) Date of Patent: Oct. 11, 2016

(54) FRAGRANCE COMPOSITION

(71) Applicant: TAKASAGO INTERNATIONAL CORPORATION, Tokyo (JP)

(72) Inventors: Hiroyuki Matsuda, Kanagawa (JP); Tomohiko Hakamata, Kanagawa (JP); Hideo Ujihara, Kanagawa (JP); Hiroki Ito, Kanagawa (JP)

(73) Assignee: TAKASAGO INTERNATIONAL CORPORATION, Tokyo (JP)

( * ) Notice: Subject to any disclaimer, the term of this patent is extended or adjusted under 35 U.S.C. 154(b) by 0 days.

(21) Appl. No.: 14/431,614

(22) PCT Filed: Sep. 30, 2013

(86) PCT No.: PCT/JP2013/076580
§ 371 (c)(1),
(2) Date: Mar. 26, 2015

(87) PCT Pub. No.: WO2014/054589
PCT Pub. Date: Apr. 10, 2014

(65) Prior Publication Data
US 2015/0275131 A1 Oct. 1, 2015

(30) Foreign Application Priority Data
Oct. 1, 2012 (JP) ................................. 2012-219613

(51) Int. Cl.
| | |
|---|---|
| *A61K 8/18* | (2006.01) |
| *A61Q 13/00* | (2006.01) |
| *C11B 9/00* | (2006.01) |
| *A61Q 5/02* | (2006.01) |
| *A61Q 19/10* | (2006.01) |
| *A61K 8/33* | (2006.01) |
| *A61Q 19/00* | (2006.01) |

(52) U.S. Cl.
CPC .............. *C11B 9/0015* (2013.01); *A61K 8/33* (2013.01); *A61Q 5/02* (2013.01); *A61Q 13/00* (2013.01); *A61Q 19/00* (2013.01); *A61Q 19/10* (2013.01)

(58) Field of Classification Search
CPC ....... C11B 9/0015; C11B 9/00; A61Q 13/00; A61Q 19/00; A61Q 8/35; A61K 8/33; A61K 8/35
USPC .......................................... 512/27, 26, 25, 1
See application file for complete search history.

(56) References Cited

U.S. PATENT DOCUMENTS

| | | | | |
|---|---|---|---|---|
| 5,753,610 A | * | 5/1998 | Harada | ................. C11B 9/0015 512/25 |
| 5,942,272 A | * | 8/1999 | Kaiser | .................... C07C 45/62 424/49 |
| 9,284,246 B2 | | 3/2016 | Ujihara et al. | |
| 2015/0218072 A1 | | 8/2015 | Ujihara et al. | |

FOREIGN PATENT DOCUMENTS

| | | |
|---|---|---|
| EP | 2894143 A1 | 7/2015 |
| JP | 8-3092 A | 1/1996 |
| JP | 8-245979 A | 9/1996 |

OTHER PUBLICATIONS

Dietmar Bartschat et al.; "Chiral Compounds of Essential Oils XXI:(E, Z)-2,3-Dihydrofarnesals—Chirospecific Analysis and Structure Elucidation of the Stereoisomers"; Phytochemical Analysis; vol. 8; No. 4; 1997; pp. 159-166.
Anna Luxova et al.; "Absolute Configuration of Chiral Terpenes in Marking Pheromones of Bumblebees and Cuckoo Bumblebees"; Chirality; vol. 16, No. 4; 2004; pp. 228-233.
Sonja Mayer et al.; "Asymmetric Counteranion-Directed Catalysis"; Angewandte Chemie International Edition; Organocatalysis; vol. 45; No. 25; 2006; pp. 4193-4195.
Search Report dated Nov. 26, 2013 issued by the International Searching Authority in counterpart International Patent Application No. PCT/JP2013/076580 (PCT/ISA/210).
Written Opinion dated Nov. 26, 2013 issued by the International Searching Authority in counterpart International Patent Application No. PCT/JP2013/076580 (PCT/ISA/237).
Communication from the European Patent Office issued May 18, 2016 in a counterpart European Application No. 13844169.6.

* cited by examiner

*Primary Examiner* — Ling Choi
*Assistant Examiner* — Jessica E Whiteley
(74) *Attorney, Agent, or Firm* — Sughrue Mion, PLLC

(57) ABSTRACT

A fragrance composition contains (3S)-(6E)-2,3-dihydrofarnesal. A chemical purity of the (3S)-(6E)-2,3-dihydrofarnesal is 90 mass % or more and an optical purity of the (3S)-(6E)-2,3-dihydrofarnesal is 50% e.e. or more. A fragrance or cosmetic contains the fragrance composition. An odor is improved by using the fragrance composition containing (3S)-(6E)-2,3-dihydrofarnesal having a chemical purity of 90 mass % or more and an optical purity of 50% e.e. or more.

10 Claims, No Drawings

FRAGRANCE COMPOSITION

TECHNICAL FIELD

The present invention relates to a fragrance composition containing (3S)-(6E)-2,3-dihydrofarnesal capable of imparting a muguet-like floral feeling to a fragrance composition and a fragrance or cosmetic containing the fragrance composition. The invention further relates to the use of (3S)-(6E)-2,3-dihydrofarnesal.

BACKGROUND ART

The aroma of a fragrance or cosmetic can be classified roughly into a floral aroma and a fruity aroma and the floral aroma can be classified into three main floral aromas, that is, (1) muguet (lily of the valley), (2) rose, and (3) jasmine. Of these, an aroma having a muguet-like floral feeling is one of traditionally favored aromas and now it is a component used for imparting naturalness or flesh feeling to many products. Essential oil components can scarcely be obtained industrially from natural muguet, and thus, synthetic materials are used for the preparation of a muguet aroma.

As such an aroma having a muguet-like floral feeling, synthetic materials such as Lilial (Givaudan S.A.), Suzaral (Takasago International Corporation), Bourgeonal (Givaudan S.A./Quest), Mayol (Firmenich S.A.), Cyclamen aldehyde (Givaudan S.A.), 2,3-Dihydrofarnesal, and 2,3-Dihydrofarnesol have been used.

Of these synthetic materials, a racemic form of 2,3-dihydrofarnesal has already been organoleptically evaluated. A mixture of the (E)-isomer and the (Z)-isomer has a flower (floral) aroma note. The (E)-isomer of the racemic form has an aldehydic fragrance with a fresh floral aroma note and reminds of a lily of the valley or another flower. It is an aroma easily harmonizing with a fresh water note, an ozone note, a marine note or the like. On the other hand, the (Z)-isomer of the racemic form has aroma intensity slightly lower than that of the (E)-isomer and it provides an odor slightly inferior in freshness as a whole, but it is known to have an aroma showing similar olfactory characteristics (Patent Document 1).

Also, it is known that in the natural world, 2,3-dihydrofarnesal exists in plants and animals. For example, it is known that 2,3-dihydrofarnesal exists in an extract of Orchids (*Aerides jarckanum*), a flower aroma component of *Citrus limon* (Non-Patent Document 1) and a pheromone component of Bumblebees and Cuckoo Bumblebees (Non-Patent Document 2).

As an example of synthesizing optically active 2,3-dihydrofarnesal, a report on the synthesis of (3R)-2,3-dihydrofarnesal by asymmetric hydrogenation of (2E,6E)-farnesal is known (Non-Patent Document 3).

CITATION LIST

Patent Document

Patent Document 1: JP-A-H08-3092

Non-Patent Documents

Non-patent Document 1: Phytochemical Analysis (1997), 8(4), pp. 159-166.
Non-patent Document 2: Chirality (2004), 16(4), pp. 228-233
Non-patent Document 3: Angewandte Chemie, International Edition (2006), 45(25), pp. 4193-4195

SUMMARY OF THE INVENTION

Problems to be Solved by the Invention

In any of the above-mentioned citation list, there is no finding on the relationship between a difference between the (S)-isomer and the (R)-isomer which are optical isomers of 2,3-dihydrofarnesal and an aroma. There is neither disclosure nor suggestion on the relationship.

A first object of the present invention therefore relates to the development of a new fragrance material that uses 2,3-dihydrofarnesal, provides a muguet-like floral fragrance which tends to be more highly favored, and is excellent in odor quality. Particularly, a first object thereof is to provide a fragrance composition having a strong floral feeling, is excellent in substantivity (long lasting property), has high performance, and is capable of expressing an excellent muguet-like odor quality, when added into fragrances or cosmetics.

A second object of the present invention is to provide a fragrance or cosmetic containing the fragrance composition.

A third object of the present invention is to provide an odor improvement method capable of imparting an aroma excellent in long lasting property, performance, and muguet-like aroma by using the fragrance composition.

Means for Solving the Problems

In order to solve the above-mentioned problems, the present inventors have carried out an intensive investigation. As a result, it has been found surprisingly that a fragrance obtained by mixing the (S)-isomer and (R)-isomer of optically active 2,3-dihydrofarnesal at a specific ratio has an excellent muguet-like aroma having a strong cyclamen-like floral feeling, excellent in long lasting property, and having high performance, leading to the completion of the present invention.

That is, the present invention relates to following [1] to [6].

[1] A fragrance composition comprising (3S)-(6E)-2,3-dihydrofarnesal having a chemical purity of 90 mass % or more and an optical purity of 50% e.e. or more.

[2] The fragrance composition according to [1], wherein the optical purity of the (3S)-(6E)-2,3-dihydrofarnesal is 70% e.e. or more.

[3] The fragrance composition according to [1] or [2], wherein the (3S)-(6E)-2,3-dihydrofarnesal is contained in an amount of from 0.001 to 40 mass %.

[4] A fragrance or cosmetic comprising the fragrance composition according to any one of [1] to [3].

[5] An odor-improving method using a fragrance composition comprising (3S)-(6E)-2,3-dihydrofarnesal having a chemical purity of 90 mass % or more and an optical purity of 50% e.e. or more.

[6] A method of imparting a floral-like aroma to a fragrance or cosmetic by using a (3S)-(6E)-2,3-dihydrofarnesal having a chemical purity of 90 mass % or more and an optical purity of 50% e.e. or more.

Advantageous Effect of the Invention

Since the (3S)-(6E)-2,3-dihydrofarnesal contained in the fragrance composition in the present invention has an optical purity of 50% e.e. or more, the fragrance composition has an excellent aroma with high performance and has characteristics superior to conventionally known muguet fragrances. The (3S)-(6E)-2,3-dihydrofarnesal having an optical purity of 50% e.e. or more to be used in the present invention produces an effect even when its amount is small, and thus, it can impart scent to fragrances or cosmetics requiring perfuming with a fragrance. Further, since it has an odor quality excellent in long lasting property, which is peculiar to muguet, it can give expansion or unity to blended fragrances and enhance a preference therefor or odor intensity. Thus, it can give a positive effect to them as a whole and can give them a natural muguet feeling.

In the present invention, therefore, a fragrance composition which is far superior to conventional muguet-like fragrances and is markedly practical can be obtained by incorporating, in the composition, (3S)-(6E)-2,3-dihydrofarnesal having an optical purity equal to or more than a predetermined optical purity.

MODE FOR CARRYING OUT THE INVENTION

The present invention will hereinafter be described in detail.

The terms "mass %" and "wt %" as used herein have the same meanings, and the terms "part(s) by mass" and "part(s) by weight" have the same meaning.

The fragrance composition in the present invention contains (3S)-(6E)-2,3-dihydrofarnesal having an optical purity of 50% e.e. or more. First, optically active 2,3-dihydrofarnesal (which may hereinafter be called "optically active DH-farnesal") will be described specifically.

2,3-Dihydrofarnesal has one asymmetric carbon in the molecule thereof, and thus, it has a (3S)-isomer and a (3R)-isomer and further, it has cis-trans isomerism due to substitution on the double bond, and thus, it has two geometric isomers, that is, (6E)-isomer and (6Z)-isomer. Thus, it has four optical isomers as shown in the following formulas (1) to (4).

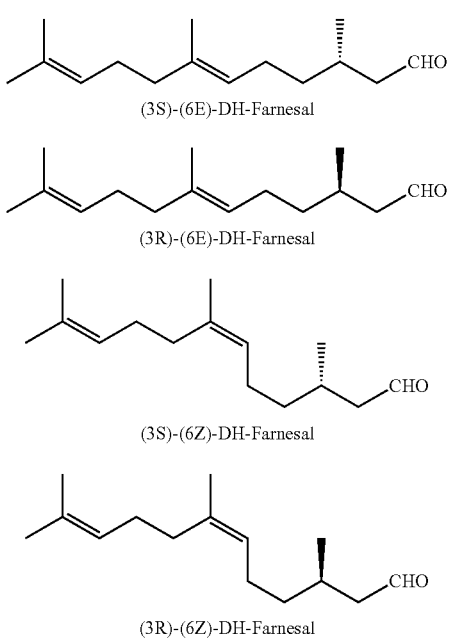

[Chem. 1]

(1) (3S)-(6E)-DH-Farnesal
(2) (3R)-(6E)-DH-Farnesal
(3) (3S)-(6Z)-DH-Farnesal
(4) (3R)-(6Z)-DH-Farnesal As described above, a mixture of four optical isomers represented by the formulas (1) to (4), respectively, which are obtained by hydrogenating a mixture of geometric isomers of a farnesal, or (6E)-dihydrofarnesal or (6Z)-dihydrofarnesal of the racemic form obtained by hydrogenating (6E)-farnesal or (6Z)-farnesal, has been conventionally used as a fragrance.

The fragrance composition in the present invention contains a predetermined amount of (−)-(3S)-(6E)-2,3-dihydrofarnesal (which may hereinafter be called "(S)-DH-farnesal" or "(S)-isomer") represented by the above formula (1) among two optically active 2,3-dihydrofarnesals which are (E)-isomers. The fragrance composition in the present invention may contain (+)-(3R)-(6E)-2,3-dihydrofarnesal (which may hereinafter be called "(R)-DH-farnesal" or "(R)-isomer") which is the other optically active 2,3-dihydrofarnesal represented by the above formula (2). A mixing ratio of the (S)-isomer and the (R)-isomer can be adjusted as needed, depending on the desired aroma.

The mixing ratio (mass ratio) of the (S)-isomer and (R)-isomer of the optically active DH-farnesal is preferably adjusted so that a ratio of the (S)-isomer is 75% or more and that of the (R)-isomer is 25% or less. When the mixing ratio falls within the above-mentioned range, a fragrance composition containing the optically active DH-farnesal has an odor quality superior to that of conventionally and frequently used muguet fragrances. In particular, it is more preferred to adjust the mixing ratio (mass ratio) of the (S)-isomer and (R)-isomer of the optically active DH-farnesal so that a ratio of the (S)-isomer is 85% or more and that of the (R)-isomer is 15% or less. It is still more preferred to adjust it so that a ratio of the (S)-isomer is 90% or more and that of the (R)-isomer is 10% or less.

When the mixing ratio falls within the above-mentioned range, the fragrance composition containing the optically active DH-farnesal has an odor quality far superior to that of conventionally known muguet fragrances.

The (S)-DH-farnesal contained in the fragrance composition in the present invention has an optical purity of 50% e.e. or more, more preferably 70% e.e. or more, still more preferably 80% e.e. or more, and particularly preferably 90% e.e. or more.

The optically active DH-farnesal contained in the fragrance composition in the present invention is a mixture of the (S)-isomer and the (R)-isomer unless the (S)-DH-farnesal has an optical purity of 100% e.e.

A fragrance composition containing a mixture obtained by mixing (S)-DH-farnesal and (R)-DH-farnesal so that the optical purity of the (S)-DH-farnesal is 50% e.e. or more (so that the amount of the (S)-isomer is 75 mass % or more) is a considerably excellent fragrance composition superior in odor quality, particularly muguet-like odor quality and long lasting property, to conventionally and frequently used muguet fragrances and capable of providing a positive effect as a whole.

The chemical purity of the (S)-DH-farnesal in the present invention is preferably 90 mass % or more, more preferably 95 mass % or more from the standpoint of an odor quality.

The chemical purity can be determined by general gas chromatography measurement.

Similarly, when the fragrance composition in the present invention contains the (R)-DH-farnesal, the chemical purity of the (R)-DH-farnesal is preferably 90 mass % or more, more preferably 95 mass % or more.

A process of producing (S)-DH-farnesal having an optical purity of 50% e.e. or more will next be described.

As a starting material for preparing the (S)-isomer of optically active DH-farnesal or a mixture of the (S)-isomer and the (R)-isomer of optically active DH-farnesal, an extract from a natural product can be used or a material obtained by a chemical synthesis method can be used.

When the extract is obtained from a natural product, the amount of the extract is very small, and thus, a material obtained by a chemical synthesis method is preferably used in order to obtain a large amount of the starting material.

When the chemical synthesis method is selected, the (S)-isomer and (R)-isomer of optically active DH-farnesal can be obtained separately, for example, by preparing a racemate, that is, an equimolar mixture of the (S)-isomer and (R)-isomer of optically active DH-farnesal in a conventional manner and then optically resolving it.

As another chemical synthesis method, examples thereof include a method in which chemically pure (6E)-farnesol or (6Z)-farnesol is asymmetrically hydrogenated using, as a catalyst, a ruthenium-optically active phosphine complex which is an (R)-isomer or (S)-isomer, thereby preparing the (S)-isomer or (R)-isomer of DH-farnesol (refer to JP-A-H08-245979), followed by oxidizing the alcohol moiety of the DH-farnesol to form a corresponding aldehyde.

Specifically, optically active (−)-(3S)-(6E)-2,3-dihydrofarnesol is synthesized by asymmetric hydrogenation of (2E,6E)-farnesol in the presence of a catalyst such as optically active ruthenium-BINAP catalyst, for example, $Ru_2Cl_4$ ((R)-T-BINAP)$_2$NEt$_3$ ((R)-T-BINAP represents (R)-2,2'-bis[di(p-tolyl)phosphino]-1,1'-binaphthyl and Et represents an ethyl group).

On the other hand, Optically active (+)-(3R)-(6E)-2,3-dihydrofarnesol is synthesized by asymmetric hydrogenation of (2E,6E)-farnesol in the presence of a catalyst such as optically active ruthenium-BINAP catalyst, for example, $Ru_2Cl_4$ ((S)-T-BINAP)$_2$NEt$_3$ ((S)-T-BINAP represents (S)-2,2'-bis[di(p-tolyl)phosphino]-1,1'-binaphthyl and Et represents an ethyl group).

(S)-DH-Farnesal or (R)-DH-farnesal can be synthesized by oxidizing the alcohol moiety of the optically active DH-farnesol, more specifically, (S)-DH-farnesol or (R)-DH-farnesol obtained by the above-described method, to form a corresponding aldehyde by an oxidation method using, for example, tetrapropylammonium perruthenate/4-methylmorpholine N-oxide or N-chlorosuccinimide/N-t-butylbenzenesulfenamide.

The chemical purity of the (S)-DH-farnesal or (R)-DH-farnesal is preferably 90 mass % or more, more preferably 95 mass % or more. When the (S)-DH-farnesal or (R)-DH-farnesal thus synthesized has a low chemical purity, it can be used after increasing its purity.

Examples of a purity increasing method include general distillation and column chromatography separation.

(3S)-(6E)-2,3-Dihydrofarnesal having a desired optical purity and to be used in the present invention can be obtained by suitably mixing the starting materials of the thus-obtained (S)-DH-farnesal and (R)-DH-farnesal, depending on an intended ratio of them.

(S)-DH-Farnesal having an intended optical purity can also be obtained by adding DH-farnesal of racemic form to the above-mentioned (S)-DH-farnesal and mixing them.

Further, a mixture having (S)-DH-farnesal and (R)-DH-farnesal at an intended mixing ratio can be prepared by adjusting reaction conditions and the like of the above-mentioned optical resolution or asymmetric synthesis.

As shown later in Examples, the (S)-isomer has an odor detection threshold (the lowest concentration perceivable by the sense of smell) smaller than that of the (R)-isomer. The optically active DH-farnesal containing at least a predetermined amount of the (S)-isomer is much superior in odor performance and odor intensity. Further, the optically active DH-farnesal containing at least a predetermined amount of the (S)-isomer has high preference and excellent and aromatic odor characteristics peculiar to muguet-like aroma and shows remarkable odor substantivity. By incorporating it into a fragrance composition, the fragrance composition having high preference can be provided. Further, addition of the optically active DH-farnesal containing at least a predetermined amount of the (S)-isomer particularly enhances the effect of the desired aroma substantivity and long lasting property of the resulting fragrance composition.

The amount of the optically active DH-farnesal containing at least a predetermined amount of the (S)-isomer, that is, the (S)-isomer or a mixture of the (S)-isomer and the (R)-isomer to be incorporated in a fragrance composition differs, depending on the kind or intended use of the fragrance composition. In general, it is appropriate to add the (S)-DH-farnesal in an amount to give a content of from 0.001 to 40 mass %, more preferably from 0.01 to 20 mass %, still more preferably from 0.1 to 10 mass %, based on the fragrance composition.

When the fragrance composition in the present invention also contains (R)-DH-farnesal, the content of the mixture of the (S)-isomer and the (R)-isomer is preferably from 0.001 to 40 mass %, more preferably from 0.01 to 20 mass %, based on the fragrance composition.

The (S)-isomer or mixture of the (S)-isomer and the (R)-isomer of the optically active DH-farnesal in the present invention themselves have a muguet-like odor quality, and thus, an odor can also be improved by using a fragrance composition containing the optically active DH-farnesal.

The composition of the fragrance composition containing the (S)-isomer or mixture of the (S)-isomer and the (R)-isomer of the optically active DH-farnesal in the present invention is not particularly limited and the fragrance composition can be prepared by adding an ordinarily used fragrance component to the (S)-isomer or mixture of the (S)-isomer and the (R)-isomer of the optically active DH-farnesal.

Examples of the ordinarily used fragrance component that can be added or used include various synthetic flavors or fragrances, natural essential oils, synthetic essential oils, citrus oils, and animal flavors or fragrances. Thus, a wide range of flavor or fragrance components can be used.

Of these flavor or fragrance components, typical examples thereof include ca-pinene, limonene, cis-3-hexenol, phenylethyl alcohol, styrallyl acetate, eugenol, rose oxide, linalool, benzaldehyde, methyl dihydrojasmonate, Tesaron (Takasago International Corporation) and the like. Flavor or fragrance components described in Arctander S. "Perfume and Flavor Chemicals" published By the author, Montclair, N.J. (U.S.A.) (1969) can also be used.

By adding the (S)-isomer or mixture of the (S)-isomer and the (R)-isomer of the optically active DH-farnesal to a natural essential oil such as bergamot oil, galbanum oil, lemon oil, geranium oil, lavender oil, or mandarin oil, it is possible to prepare a novel fragrance composition providing, in addition to an odor or flavor which the natural essential oil originally has, a mild, rich, fresh, and high preference and having enhanced diffusivity and retention property and substantivity.

In the present invention, one or more of the other ordinarily-used fragrance retaining agent may be incorporated into a compound such as the (S)-isomer or mixture of the (S)-isomer and the (R)-isomer of the optically active DH-farnesal, a fragrance composition containing the compound, or the fragrance composition for fragrances or cosmetics.

As the other fragrance retaining agent, for example, ethylene glycol, propylene glycol, dipropylene glycol, glycerin, hexyl glycol, benzyl benzoate, triethyl citrate, diethyl phthalate, Hercolyn (methyl abietate), or a medium chain fatty acid triglyceride may be used in combination.

Although no particular limitation is imposed on a fragrance or cosmetic to which aroma can be imparted by using the (S)-isomer or mixture of the (S)-isomer and the (R)-isomer of the optically active DH-farnesal in the present invention or a fragrance composition containing the compound, examples thereof include fragrance products, basic cosmetics, finish cosmetics, hair cosmetics, suntan cosmetics, medicated cosmetics, hair care products, soaps, body washers, bath agents, detergents, fabric softeners, cleaning agents, kitchen detergents, bleaching agents, aerosols, deodorants and air fresheners, and household goods.

Examples of the fragrance products include perfume, eau de parfum, eau de toilette, eau de cologne and the like;

examples of the basic cosmetics include face wash cream, vanishing cream, cleansing cream, cold cream, massage cream, milky lotion, skin lotion, beauty essence, facial mask, makeup remover and the like;

examples of the finish cosmetics include foundation, powder foundation, solid foundation, talcum powder, lipstick, lip balm, blush, eyeliner, mascara, eye shadow, eyebrow pencil, eye pack, nail enamel, enamel remover and the like;

examples of the hair cosmetics include pomade, brilliantine, setting lotion, hair stick, hair solid, hair oil, hair treatment, hair cream, hair tonic, hair liquid, hair spray, bandlin, revitalizing hair tonic, hair dye and the like;

examples of the suntan cosmetics include suntan product, sunscreen product and the like, examples of the medicated cosmetics include antiperspirant, after-shaving lotion and gel, permanent wave agent, medicated soap, medicated shampoo, medicated skin cosmetic and the like;

examples of the hair care products include shampoo, rinse, conditioning shampoo, conditioner, treatment, hair pack and the like;

examples of the soaps include toilet soap, bath soap, perfume soap, transparent soap, synthetic soap and the like;

examples of the body washers include body soap, body shampoo, hand soap, face cream and the like; examples of the bath agents include bath additive (bath salt, bath tablet, bath liquid and the like), agent for foam bath (agent for bubble bath and the like), bath oil (bath perfume, bath capsule and the like), milk bath, bath gel, bath cube and the like;

examples of the detergents include clothing heavy-duty detergent, clothing light-duty detergent, liquid detergent, washing soap, compact detergent, powder soap and the like;

examples of the fabric softeners include softener, furniture care and the like;

examples of the cleaning agents include cleanser, house cleaner, toilet cleaner, bath room cleaner, glass cleaner, mold removing agent, drainage pipe cleaner and the like;

examples of the kitchen detergents include kitchen soap, kitchen synthetic soap, dishwash soap and the like;

examples of the bleaching agents include oxidation-based bleaching agent (chlorine-based bleaching agent, oxygen-based bleaching agent and the like), reduction-based bleaching agent (sulfur-based bleaching agent and the like), optical bleaching agent and the like;

examples of the aerosols include spray type aerosols, powder spray type aerosols and the like;

examples of the deodorants and air fresheners include solid type one, gel type one, liquid type one (water, oil) and the like; and examples of the household goods include tissue paper, toilet paper and the like.

The (S)-isomer or mixture of the (S)-isomer and the (R)-isomer of the optically active DH-farnesal can be provided in the form of a compound or a mixture itself.

It can also be provided in a liquid form dissolved in an alcohol, a polyalcohol such as propylene glycol, glycerin or dipropylene glycol, or an ester such as triethyl citrate, benzyl benzoate or diethyl phthalate; in a natural rubber form such as gum arabic or tragacanth gum; in an emulsified form obtained by emulsifying with an emulsifier such as glycerin fatty acid ester or sucrose fatty acid ester; in a powder form coated with a carrier such as a natural rubber such as gum arabic, gelatin or dextrin; in a solubilized or dispersed form obtained by solubilizing or dispersing with a surfactant such as nonionic surfactant, anionic surfactant, cationic surfactant or amphoteric surfactant; or in a microcapsule form obtained by treating with an encapsulation agent. Any form can be selected, depending on the intended use.

The fragrance composition may also be used after having been included in an inclusion agent such as cyclodextrin in order to impart stability or sustained release property to the fragrance composition. The inclusion agent may be selected as needed, depending on the form of the final product, for example, liquid, solid, gel, mist, or aerosol.

Although an addition amount of the compound which is the (S)-isomer or (S)-isomer/(R)-isomer mixture of the optically active DH-farnesal or addition amount of a fragrance composition containing the compound to a final product such as fragrance product cannot be defined because it is increased or decreased arbitrarily, depending on an object for which it is used or condition in which it is used, or expected advantage or effect, it is generally from about 0.00001 to 20 mass %.

A utilization or application method of the fragrance composition containing (S)-DH-farnesal in the present invention is not particularly limited and it can be used in any of conventionally known utilization or application methods of fragrance. The composition can give an excellent odor quality to various fragrances or cosmetics. Improvement of odor by using the (S)-DH-farnesal-containing fragrance composition in the present invention is also one of the characteristics of the present invention.

EXAMPLES

The present invention will hereinafter be described specifically by examples. The present invention is not limited by them. Various changes or modifications may be added without departing from the scope of the present invention. With regard to the unit of the formulation described below, "%" means "mass %" and a composition ratio means a mass ratio, unless otherwise particularly stated.

Various analyses of a product obtained in the following synthesis examples were performed using the following apparatuses or devices.

Identification of compound: nuclear magnetic resonance apparatus (NMR): AVANCE III Model 500 (500 MHz, manufactured by Bruker Corporation)

Composition analysis: gas chromatograph mass spectrometer: GCMS-QP2010 (manufactured by Shimadzu Corporation)

Column: BC-Wax (50 m×0.25 mmID)
Optical purity measurement: Gas chromatograph GC-2010 (manufactured by Shimadzu Corporation)
Column: BGB-174 (30 m×0.25 mmID)
Optical purity measurement: polarimeter: P-1020 (manufactured by JASCO Corporation)

Synthesis Example 1

Synthesis of (6E)-2,3-dihydrofarnesol

In a nitrogen atmosphere, 6.66 g (30 mmol) of farnesol (having a (2E,6E)-form, a (2E,6Z)-form, a (2Z,6E)-form, and a (2Z,6Z)-form at a ratio of 1:1:1:1, product of Takasago International Corporation) and 0.3 g of Ru-carbon (5% supported product) were placed in a 100 ml autoclave, followed by sufficiently purging with nitrogen. Then, 33 ml of methanol was added thereto in a nitrogen atmosphere. After purging with hydrogen, the hydrogen pressure was set at 40 atm and the mixture was stirred at 120° C. for 16 hours. After completion of the reaction, a portion of the reaction mixture was taken out and a conversion ratio of it was measured by gas chromatography. As a result, the conversion ratio was 100%, and it was confirmed that the hydrogenation progressed 100%.

The reaction liquid thus obtained was concentrated under reduced pressure, thereby obtaining 5.2 g of a fraction thereof. Analysis of the composition by gas chromatography revealed that it contained 52% of a (6E)-form and 48% of a (6Z)-form. A 3 g-portion of the fraction was treated with silver nitrate-supported silica gel column chromatography, thereby obtaining 0.6 g of a cis-form (Z-form)-rich fraction (85% of (6Z)-2,3-dihydrofarnesol and 15% of (6E)-2,3-dihydrofarnesol).

[Synthesis 2] Synthesis of (6E)-2,3-dihydrofarnesol

In a nitrogen atmosphere, 6.66 g (30 mmol) of trans-farnesol ((2E,6E)-form/(2Z,6E)-form=99/1, product of Takasago International Corporation) and 0.3 g of Ru-carbon (5% supported product) were placed in a 100 ml autoclave, followed by sufficiently purging with nitrogen. After addition of 33 ml of methanol in a nitrogen atmosphere and purging with hydrogen, the hydrogen pressure was set at 40 atm and the mixture was stirred at 120° C. for 16 hours. After completion of the reaction, a portion of the reaction mixture was taken out and a conversion ratio of it was measured by gas chromatography. The conversion ratio was 100%.

The reaction liquid thus obtained was concentrated under reduced pressure, thereby obtaining a fraction. Analysis of the composition by gas chromatography revealed that it contained 99% or more of (6E)-2,3-dihydrofarnesol.

[Synthesis 3] Synthesis of (3S)-(6E)-2,3-dihydrofarnesol

In a nitrogen atmosphere, 10.0 g (224.9 mmol) of farnesol ((2E,6E)-form/(2Z,6E)-form=98/2, product of Takasago International Corporation) and 81.1 mg (0.09 mmol) of $Ru_2Cl_4$ ((R)-T-BINAP)$_2$NEt$_3$ ((R)-T-BINAP represents (R)-2,2'-bis[di(p-tolyl)phosphino]-1,1'-binaphthyl and Et represents ethyl group, product of Takasago International Corporation) were placed in a 200 ml autoclave, followed by sufficiently purging with nitrogen. After addition of 50 ml of methanol in a nitrogen atmosphere and purging with hydrogen, the hydrogen pressure was set at 40 atm and the mixture was stirred at room temperature for 16 hours. After completion of the reaction, a portion of the reaction mixture was taken out and a conversion ratio of it was measured by gas chromatography. The conversion ratio was 100%.

The reaction liquid thus obtained was concentrated under reduced pressure and then the crude product thus obtained was distilled under reduced pressure, thereby obtaining 8.3 g (yield: 82%) of (3S)-(6E)-2,3-dihydrofarnesol having a chemical purity of 96%.

The compound obtained in Synthesis Example 3 had an optical rotation of −4.00° ($[\alpha]_D^{23}$ −4.00° (C=20, chloroform)), which revealed that it had an optical purity of 91% e.e. (literature value: calculated based on Acta. Chem. Scand., 1971, Vol. 25, pp. 1685-1694). With regard to the trans form (E-form) and cis form (Z-form), the trans form (6-position) of the starting material was maintained and the ratio of the (6E)-form was 100%.

[Synthesis 4] Synthesis of (3R)-(6E)-2,3-dihydrofarnesol

A reaction was conducted in a procedure similar to that employed in Synthesis Example 3 except that $Ru_2Cl_4$ ((S)-T-BINAP)$_2$NEt$_3$ (product of Takasago International Corporation) was used instead of $Ru_2Cl_4$ ((R)-T-BINAP)$_2$NEt$_3$, thereby obtaining 8.5 g (yield: 84%) of (3R)-(6E)-2,3-dihydrofarnesol having a chemical purity of 96% as analyzed by gas chromatography. The compound thus obtained had an optical rotation of +3.78° ($[\alpha]_D^{23}$ +3.78° (C=20, chloroform)), which revealed that it had an optical purity of 86% e.e.

Synthesis Example 5

Synthesis of (3S)-(6E)-2,3-dihydrofarnesal

Molecular Sieves 4A (13.4 g, 0.5 g/mmol), 6.0 g (26.7 mmol) of the (3S)-(6E)-2,3-dihydrofarnesol obtained in Synthesis Example 3, and 6.3 g (53.5 mmol) of 4-methyl-morpholin-N-oxide were mixed in dichloromethane (150 ml) and acetonitrile (18 ml). The resulting mixture was stirred at room temperature for 30 minutes. To the reaction mixture was added 0.5 g (1.3 mmol) of tetrapropylammonium perruthenate. The resulting mixture was stirred at room temperature for 2 hours. The reaction liquid was filtered through Celite and the solvent was distilled off under reduced pressure. The residue thus obtained was purified by silica gel column chromatography (hexane/ethyl acetate=97/3), thereby obtaining 2.7 g (yield: 45%) of (3S)-(6E)-2,3-dihydrofarnesal having a chemical purity of 96% and an optical purity of 91% e.e. as a colorless oily substance.

Synthesis Example 6

Synthesis of (3R)-(6E)-2,3-dihydrofarnesal

A reaction was conducted in a procedure similar to that employed in Synthesis Example 5 except that the (3R)-(6E)-2,3-dihydrofarnesol obtained in Synthesis Example 4 was used instead of the (3S)-(6E)-2,3-dihydrofarnesol. As a result of analysis by gas chromatography, 5.7 g (yield: 49%) of (3R)-(6E)-2,3-dihydrofarnesal having a chemical purity of 98% and an optical purity of 86% e.e. was obtained as a colorless oily substance.

Synthesis Example 7

Synthesis of (6E)-2,3-dihydrofarnesal

A reaction was conducted in a procedure similar to that employed in Synthesis Example 5 except that the (6E)-2,3-dihydrofarnesol obtained in Synthesis Example 2 was used instead of the (3S)-(6E)-2,3-dihydrofarnesol. As a result of analysis by gas chromatography, 5.7 g (yield: 49%) of (6E)-2,3-dihydrofarnesal having a chemical purity of 98% was obtained as a colorless oily substance.

<Measurement of Odor Detection Threshold>

The odor detection threshold of the (3S)-(6E)-2,3-dihydrofarnesal ((S)-form) obtained in Synthesis Example 5 and the (3R)-(6E)-2,3-dihydrofarnesal ((R)-form) obtained in Synthesis Example 6 was measured in the conventional method (refer to Hirotoshi Tamura: AROMA RESEARCH, Vol. 1, No. 3, pp. 28-36 (2000)). The results are shown below.

((S)-form): 2.7 ppm
((R)-form): 14.9 ppm

The results show that the detection threshold of the (S)-form is not more than 1/5 time that of the (R)-form, and it was found that the (S)-form is far superior to the (R)-form in odor intensity.

Preparation Examples 1 to 7

Preparation of Compounds 1 to 7 and Evaluation of their Odor Quality

The optically active 2,3-dihydrofarnesals obtained in Synthesis Example 5 and 6 were mixed in a ratio shown in Table 1, thereby obtaining Compounds 1 to 7 (Preparation Examples 1 to 7). Compounds 1 to 7 attached to the neck of a bottle and a filter paper were organoleptically evaluated by four perfumers having at least ten years' experience. Evaluation results are shown in Table 1.

In Table 1, S represents (S)-DH-farnesal and R represents (R)-DH-farnesal.

TABLE 1

| Compound Name | S:R ratio (mass ratio) | Optical purity (% e.e.) | Chemical purity (mass %) | Odor |
|---|---|---|---|---|
| Compound 1 | S alone | 91 | 96% | It falls within the category of Cyclamen-Muguet. Its fresh floral note reminds of aroma of odorous cyclamen. It leaves an impression that its aroma appears with light diffusivity. Having odor intensity, it shows very good results. |
| Compound 2 | 90:10 | 80 | 96% | It provides an improved odorous cyclamen-like fresh feeling peculiar to the S-form. Having odor intensity, it shows very good results in odor quality. |
| Compound 3 | 85:15 | 70 | 96% | Due to well-balance between the thickness of the R-form and the fresh diffusivity of the S-form, it provides a gorgeous floral feeling. It shows very good results. |
| Compound 4 | 75:25 | 50 | 97% | It has a natural cyclamen-like character. Having both quality and performance, it shows fairly good results. |
| Compound 5 | 70:30 | 40 | 97% | The feeling that the R-form has evoked, that is, aroma mass lingering around the bottom seems to float up. There seems to be an influence of character of the S-form from the standpoint of odor quality. Following the odor quality of racemic form, it still provides a slightly sticky impression. |
| Compound 6 | 50:50 | 0 | 98% | Compared with the R-form, it provides a muguet-like floral feeling more and the aroma is diffused more, though slightly. It still provides a sticky impression. It is not so rich in fresh feeling and its performance seems to be dominated by the R-form. |
| Compound 7 | R alone | 86 | 98% | It provides an ozone-like floral impression. Its aroma is slightly heavy, oily, and sticky. It provides a thickness but the aroma mass seems to linger around the bottom. It has no value as a fragrance. |

Example 1A and Comparative Example 1A

Preparation of a Fragrance Composition for Perfume

A fragrance composition for perfume was prepared by the conventional method based on the formulation shown below in Table 2.

TABLE 2

| Formulation | (part by mass) |
|---|---|
| α-Amylcinnamic aldehyde | 120 |
| Benzyl acetate | 40 |
| L-Citronellal | 3 |
| Citronellol | 100 |
| Cyclamen aldehyde | 20 |
| L-Dihydrofarnesol | 30 |
| Diisopropylene glycol | 25 |
| Indole | 2 |
| KOVANOL (registered trademark) (product of Takasago International Corporation) | 300 |
| Linalool | 60 |
| Phenyl ethyl alcohol | 250 |
| SANTALEX T (registered trademark) (product of Takasago International Corporation) | 20 |
| Terpineol | 30 |
| Optically active dihydrofarnesal (Compound 2 or Compound 6) | 30 |
| Total | 1030 |

According to the formulation of Example 1A, a fragrance composition for perfume was prepared using a mixture of (S)-form/(R)-form (=90/10), that is, Compound 2 as the optically active DH-farnesal.

According to the formulation of Comparative Example 1A, a fragrance composition for perfume was prepared using a racemic form of DH-farnesal ((S)-form/(R)-form=50/50), that is Compound 6, as the optically active DH-farnesal.

Organoleptic evaluation of Example 1A and Comparative Example 1A was performed by nine expert panelists having at least five years' experience. Compared with the fragrance composition for perfume obtained using the racemic form formulation in Comparative Example 1A, the fragrance composition for perfume obtained using the mixture formulation of the optically active DH-farnesal ((S)-form/(R)-form=90/10) in Example 1A was superior in any of odor intensity, naturalness and fresh feeling in evaluation results by all the panelists. The fragrance composition for perfume obtained in Comparative Example 1A was evaluated to have an aroma lacking sharpness or an artificial aroma, while the fragrance composition for perfume obtained in Example 1A earned excellent evaluation from all of the nine panelists, for example, it had a naturalness, a fresh feeling, a depth feeling, or a strong cyclamen-like white floral feeling.

Example 1B and Comparative Example 1B

Preparation of Cosmetic Cream

Cosmetic creams were prepared using the fragrance compositions for perfume obtained in Example 1A and Comparative Example 1A (Example 1B and Comparative Example 1B), respectively. The components of each of the cosmetic creams are shown below in Table 3.

TABLE 3

| Component | Mass % |
|---|---|
| Stearyl alcohol | 6.0 |
| Stearic acid | 2.0 |
| Hydrogenated lanoline | 4.0 |
| Squalene | 9.0 |
| Octyl decanol | 10.0 |
| Glycerin | 6.0 |
| Polyethylene glycol 1500 | 4.0 |
| Polyoxyethylene (25) cetyl ether | 3.0 |
| Monostearic acid glycerin | 2.0 |
| Methyl paraben | Moderate amount |
| Ethyl paraben | Moderate amount |
| Fragrance composition for perfume (Example 1A or Comparative Example 1A) | 0.1 |
| Purified water | Balance |
| Total | 100.0 |

Evaluation Method of Example 1B and Comparative Example 1B

The cosmetic cream of Comparative Example 1B was applied to the back of a left hand and an equal amount of the cosmetic cream of Example 1B was applied to the back of a right hand. The odor immediately after application and that remaining three hours after application were organoleptically evaluated as in Example 1A.

All of the nine expert panelists answered that the cosmetic cream of Example 1B containing the mixture of the optically active DH-farnesal ((S)-form/(R)-form=90/10), that is Compound 2, had a fresh floral feeling having intensity and reminding of a typical aroma of odorous cyclamen and the compound succeeded in imparting, to the cream, a muguet feeling of very good impression that appears with light diffusivity, in both cases of immediately after application and after three hours after application.

The cosmetic cream of Comparative Example 1B based on the racemic form formulation which was Compound 6 provided only a sticky impression and a muguet feeling poor in fresh feeling.

Example 2A and Comparative Example 2A

Preparation of Fragrance Composition for Shampoo

A fragrance composition for shampoo was prepared by the conventional method based on the formulation shown below in Table 4.

TABLE 4

| Formulation | (part by mass) |
|---|---|
| Benzyl acetate | 120 |
| Citronellol | 40 |
| Citronellyl acetate | 40 |
| Cyclogarvanate | 30 |
| Cyclamen aldehyde | 15 |
| α-Damascone | 6 |
| γ-Decalactone | 4 |
| GALAXOLIDE (registered trademark) (product of International Flavors & Fragrances) 50 BB | 30 |
| HEDIONE (registered trademark) (product of Firmenich) | 150 |
| HELIOBOUQUET (registered trademark) (product of Takasago International Corporation) | 150 |
| Heliotropine | 20 |
| Cis-3-hexen-1-ol | 15 |
| Cis-3-hexenyl salicylate | 20 |
| Hexyl salicylate | 30 |
| Lemon CP oil | 50 |
| Lilial | 50 |
| Linalool | 80 |
| ORBITONE (registered trademark) (product of Takasago International Corporation) | 80 |
| Optically active dihydrofarnesal (Compound 3 or Compound 6) | 10 |
| Dipropylene glycol | 90 |
| Total | 1030 |

According to the formulation of Example 2A, a fragrance composition for shampoo was prepared using a mixture of (S)-form/(R)-form (=85/15), that is, Compound 3 as the optically active DH-farnesal.

According to the formulation of Comparative Example 2A, a fragrance composition for shampoo was prepared using a racemic form ((S)-form/(R)-form=50/50), that is, Compound 6 as the optically active DH-farnesal.

Example 2B and Comparative 2B

Preparation of Shampoo

A shampoo was prepared by using the fragrance composition for shampoo prepared in Example 2A or Comparative Example 2A, stirring the components listed below in Table 5 under heat at 80° C. until the mixture became uniform, and then cooling the resulting mixture to 35° C. (Example 2B, Comparative Example 2B).

TABLE 5

| Component | Mass % |
|---|---|
| Sodium lauryl sulfate | 40.00 |
| Disodium N-coconut oil faty acid acyl-N-carboxymethoxyethyl-N-carboxymethylethylenediamine | 10.00 |
| Coconut oil fatty acid diethanolamide (2) | 2.00 |
| Butylene glycol | 2.00 |
| Citric cid | 0.35 |
| Sodium chloride | 0.10 |
| Methyl paraben | 0.20 |
| Propyl paraben | 0.10 |
| Tetrasodium edetate | 0.10 |

TABLE 5-continued

| Component | Mass % |
|---|---|
| Fragrance composition (Example 2A or Comparative Example 2A) | 0.50 |
| Purified water | Balance |
| Total | 100.0 |

Evaluation Method of Example 2B and Comparative Example 2B

A uniform human hair bundle (20 g) was immersed in 50 ml of warm water of 40° C. to wet it with the warm water for 20 minutes and then was shampooed with the shampoo (1 g) of Example 2B or Comparative Example 2B. The human hair bundle was taken out, dehydrated, rinsed with 100 ml of warm water, and then dehydrated again. One hour after drying, the odor emitted from the hair was organoleptically evaluated as in Example 1A.

Organoleptic Evaluation Results of Examples 2A and 2B and Comparative Examples 2A and 2B Eight of the nine expert panelists answered that the fragrance composition of Example 2A and the shampoo of Example 2B, each containing Compound 3 (the mixture of optically active DH-farnesal ((S)-form/(R)-form=85/15)), had a muguet feeling well-balanced between a thickness and fresh diffusivity and felt as a gorgeous floral feeling.

On the other hand, the fragrance composition of Comparative Example 2A and the shampoo of Comparative Example 2B each based on the formulation of Compound 6 (racemic form) had only a sticky impression and a muguet feeling with weak fresh feeling.

Example 3A and Comparative Example 3A

Preparation of Fragrance Composition for Body Shampoo

A fragrance composition for body shampoo was prepared by the conventional method based on the formulation shown below in Table 6.

TABLE 6

| Formulation | (part by mass) |
|---|---|
| Undecanal | 12 |
| Allyl caproate | 20 |
| Benzyl acetate | 40 |
| Citronellol | 50 |
| Coumarin | 30 |
| Tricyclodecenyl acetate | 80 |
| α-Damascone | 5 |
| GALAXOLIDE (registered trademark) (product of International Flavors & Fragrances) 50 BB | 300 |
| Geraniol | 80 |
| Linalool | 100 |
| Manzanate | 8 |
| Myrac aldehyde | 20 |
| Rose oxide | 2 |
| Triplal | 3 |
| Verdox | 100 |
| VERTENEX (registered trademark) (product of International Flavors & Fragrances) | 40 |
| VERTENEX (registered trademark) (product of International Flavors & Fragrances) | 20 |
| Optically active dihydrofarnesal (Compound 4 | 20 |

TABLE 6-continued

| Formulation | (part by mass) |
|---|---|
| or Compound 6) | |
| Dipropylene glycol | 8 |
| Total | 1010 |

According to the formulation of Example 3A, a fragrance composition for body shampoo was prepared using Compound 4 (mixture of (S)-form/(R)-form (=75/25)) as the optically active DH-farnesal.

According to the formulation of Comparative Example 3A, a fragrance composition for body shampoo was prepared using Compound 6 (racemic form ((S)-form/(R)-form=50/50)) as the optically active DH-farnesal.

Example 3B and Comparative Example 3B

Preparation of Body Shampoo

Body shampoos were prepared using the fragrance compositions for body shampoo prepared in Example 3A and Comparative Example 3A, respectively (Example 3B and Comparative Example 3B). The components of the body shampoos are shown below in Table 7.

TABLE 7

| Component | Mass % |
|---|---|
| Dibutylhydroxytoluene | 0.05 |
| Methyl paraben | 0.10 |
| Propyl paraben | 0.10 |
| Tetrasodium edetate | 0.10 |
| Potassium chloride | 0.20 |
| Glycerin | 5.00 |
| Coconut oil fatty acid diethanolamide (2) | 3.00 |
| Sodium polyoxyethylene lauryl ether acetate (3E.O.) (30%) | 10.00 |
| Coconut oil fatty acid amidopropylbetaine solution (34%) | 25.00 |
| Potassium myristate (40%) | 25.00 |
| Fragrance composition (Example 3A or Comparative Example 3A) | 0.50 |
| Purified water | Balance |
| Total | 100.0 |

Evaluation Method of Example 3B and Comparative Example 3B

After washing the palm of the hand with 50 ml of warm water of 40° C., it was washed with the body shampoo (1 g) of Example 3B or Comparative Example 3B. The palm of the hand was rinsed with 100 ml of warm water and then dried with a dry towel. The odor emitted from the palm of the hand was organoleptically evaluated as in Example 1A.

Organoleptic Evaluation Results of Examples 3A and 3B and Comparative Examples 3A and 3B Seven of nine expert panelists answered that the fragrance composition of Example 3A and the body shampoo of Example 3B, each containing the mixture of the optically active DH-farnesal ((S)-form/(R)-form=75/25), that is Compound 4, had a muguet feeling having a natural cyclamen-like character and having both a quality and performance.

On the other hand, the fragrance composition of Comparative Example 3A and the body shampoo of Comparative Example 3B, each based on the racemic form formulation, that is Compound 6, had only a sticky impression and a muguet feeling with weak fresh feeling.

Example 4A and Comparative Example 4A

Preparation of Fragrance Composition for Detergent

A fragrance composition for detergent was prepared by the conventional method based on the formulation shown below in Table 8.

TABLE 8

| Formulation | (part by mass) |
| --- | --- |
| Ambroxan | 2 |
| L-Citronellylnitrile | 20 |
| CYCLAPROP (registered trademark) (product of International Flavors & Fragrances) | 60 |
| α-Damascone | 2 |
| Dihydromyrcenol | 40 |
| Dimethyl benzyl carbinyl acetate | 30 |
| Heliotropine | 10 |
| Lemon oil | 40 |
| Lilial | 150 |
| Linalool | 80 |
| Manzanate | 20 |
| Nopyl acetate | 80 |
| POIRENATE | 20 |
| Rose base | 100 |
| Rose oxide | 1 |
| Tonalid | 30 |
| Triplal | 5 |
| Verdox | 60 |
| Optically active dihydrofarnesal (Compound 1 or Compound 5) | 15 |
| Dipropylene glycol | 35 |
| Total | 800 |

According to the formulation of Example 4A, a fragrance composition for detergent was prepared using Compound 1 ((S)-form of optically active DH-farnesal).

According to the formulation of Comparative Example 4A, a fragrance composition for detergent was prepared using Compound 5 (a mixture of optically active DH-farnesal ((S)-form/(R)-form=70/30)).

Example 4B and Comparative Example 4B

Preparation of Powdery Detergent

Powdery detergents were prepared using the fragrance compositions for detergent prepared in Example 4A or Comparative Example 4A, respectively (Example 4B and Comparative Example 4B). Components of the powdery detergents are shown below in Table 9.

TABLE 9

| Component | Mass % |
| --- | --- |
| $C_{14-15}$ Alkylethoxysulfonic acid | 5.5 |
| $C_{12-13}$ Linear alkylsulfonic acid | 12.7 |
| $C_{12-13}$ Alkyl ethoxylate | 0.5 |
| Aluminosilicate (76%) | 25.4 |
| Soap | 3.0 |
| Zeolite | 23.0 |
| Sodium silicate | 1.0 |
| Sodium carbonate | Balance |
| Sodium sulfate | 4.0 |

TABLE 9-continued

| Component | Mass % |
| --- | --- |
| Sodium sulfite | 1.0 |
| Enzyme | 1.0 |
| Copolymer of acrylic acid and maleic acid | 2.5 |
| Fluorescent dye | 0.3 |
| Silicone | 0.3 |
| Fragrance composition (Example 4A or Comparative Example 4A) | 0.3 |
| Water | 3.0 |
| Total | 100.0 |

Evaluation Method of Example 4B and Comparative Example 4B

A towel was washed with each of the powdery detergents of Example 4B and Comparative Example 4B, followed by dehydration treatment. The odor emitted from the resulting towel at that time was organoleptically evaluated as in Example 1A.

Organoleptic Evaluation Results of Examples 4A and 4B and Comparative Examples 4A and 4B All of the nine expert panelists answered that the fragrance composition of Example 4A and the powdery detergent of Example 4B, each containing Compound 1 ((S)-form of optically active DH-farnesal), had a fresh floral feeling reminding them of an aroma of odorous cyclamen and a very good muguet feeling having an impression that an aroma appeared with light diffusivity and also having intensity.

On the other hand, the fragrance composition of Comparative Example 4A and the powdery detergent of Comparative Example 4B, each containing the mixture of optically active DH-farnesal ((S)-form/(R)-form=70/30), that is Compound 5, had only a muguet-like feeling with slightly sticky impression, following the odor quality of racemic form, and had a sense of stagnation around the bottom which was evoked by the simple substance of the R-form, although an odor quality influenced by the character of the S-form was felt.

Example 5A and Comparative Example 5A

Preparation of Fragrance Composition for Softener

A fragrance composition for softener was prepared by the conventional method based on the formulation shown below in Table 10.

TABLE 10

| Formulation | (part by mass) |
| --- | --- |
| Ambroxan | 3 |
| CASHMERAN (registered trademark) (product of International Flavors & Fragrances) | 10 |
| Coumarin | 60 |
| Dimethyl benzyl carbinyl acetate | 30 |
| Ethyl 2-methylbutyrate | 10 |
| Ethyl cinnamate | 20 |
| Ethyl linalool | 40 |
| EXALTOLIDE (registered trademark) (product of Firmenich) | 200 |
| Geraniol | 30 |
| cis-3-Hexen-1-ol | 2 |
| Hexyl cinnamic aldehyde | 200 |

TABLE 10-continued

| Formulation | (part by mass) |
|---|---|
| LEVOSANDOL (registered trademark) (product of Takasago International Corporation) | 10 |
| γ-Methylionone | 40 |
| L-muscone (product of Takasago International Corporation) | 5 |
| ORBITONE (registered trademark) (product of Takasago International Company) | 60 |
| Rosephenone | 20 |
| γ-Undecalactone | 40 |
| Vanillin | 20 |
| Optically active dihydrofarnesal (Compound 4 or Compound 6) | 15 |
| Dipropylene glycol | 85 |
| Total | 900 |

According to the formulation of Example 5A, a fragrance composition for softener was prepared using Compound 4 (mixture of (S)-form/(R)=75/25) as the optically active DH-farnesal.

According to the formulation of Comparative Example 5A, a fragrance composition for softener was prepared using Compound 6 (racemic form ((S)-form/(R)-form=50/50)) as the optically active DH-farnesal.

Example 5B and Comparative Example 5B

Preparation of Softener for Clothes

Softeners for clothes were prepared using the fragrances composition for softener prepared in Example 5A and Comparative Example 5A, respectively (Example 5B and Comparative Example 5B). The components of the softener for clothes are shown below in Table 11.

TABLE 11

| Component | Mass % |
|---|---|
| Dialkyldimethylammonium chloride | 15.0 |
| POE (30) lauryl ether | 3.0 |
| Fatty acid | 1.0 |
| Dimethylpolysiloxane | 0.5 |
| Ethylene glycol | 5.0 |
| Antiseptic | Moderate amount |
| Sequestering agent | Moderate amount |
| Fragrance composition (Example 5A or Comparative Example 5A) | 0.3 |
| Ion exchange water | Balance |
| Total | 100.0 |

Evaluation Method of Example 5B and Comparative Example 5B

A towel washed with a fragrance-free detergent was immersed for 10 minutes in the softener for clothes obtained in Example 5B or Comparative Example 5B, followed by dehydration treatment. The odor emitted from the towel was then organoleptically evaluated as in Example 1A.

Organoleptic Evaluation Results of Examples 5A and 5B and Comparative Examples 5A and 5B Seven of the nine expert panelists answered that the fragrance composition of Example 5A and the softener for clothes obtained in Example 5B, each containing Compound 4 (the mixture of the optically active DH-farnesal ((S)-form/(R)-form)=75/25) had a muguet feeling having a natural cyclamen-like character and having both quality and performance.

On the other hand, the fragrance composition of Comparative Example 5A and the softener for clothes obtained in Comparative Example 5B, each based on the racemic form formulation, that is Compound 6, had only a muguet feeling with sticky impression and weak fresh feeling.

While the present invention has been described in detail and with reference to specific embodiments thereof, it will be apparent to one skilled in the art that various changes and modifications can be made therein without departing from the spirit and scope thereof. The present application is based on Japanese Patent Application No. 2012-219613 filed on Oct. 1, 2012, the contents of which are incorporated herein by reference.

The invention claimed is:

1. A fragrance composition comprising (3S)-(6E)-2,3-dihydrofarnesal having a chemical purity of 90 mass % or more and an optical purity of 50% e.e. or more.

2. The fragrance composition according to claim 1, wherein the optical purity of the (3S)-(6E)-2,3-dihydrofarnesal is 70% e.e. or more.

3. The fragrance composition according to claim 2, wherein the (3S)-(6E)-2,3-dihydrofarnesal is contained in an amount of from 0.001 to 40 mass %.

4. A fragrance or cosmetic comprising the fragrance composition according to claim 1.

5. An odor-improving method using a fragrance composition comprising (3S)-(6E)-2,3-dihydrofarnesal having a chemical purity of 90 mass % or more and an optical purity of 50% e.e. or more.

6. A method of imparting a floral-like aroma to a fragrance or cosmetic, the method comprising incorporating (3S)-(6E)-2,3-dihydrofarnesal having a chemical purity of 90 mass % or more and an optical purity of 50% e.e. or more into the fragrance or cosmetic.

7. The fragrance composition according to claim 1, wherein the (3S)-(6E)-2,3-dihydrofarnesal is contained in an amount of from 0.001 to 40 mass %.

8. A fragrance or cosmetic comprising the fragrance composition according to claim 2.

9. A fragrance or cosmetic comprising the fragrance composition according to claim 3.

10. A fragrance or cosmetic comprising the fragrance composition according to claim 7.

* * * * *